United States Patent
Li et al.

(10) Patent No.: US 10,954,246 B2
(45) Date of Patent: Mar. 23, 2021

(54) COMPOUND OF EOC315 MOD.I CRYSTAL FORM AND PREPARATION METHOD THEREOF

(71) Applicant: Taizhou EOC Pharma Co., Ltd., Taizhou (CN)

(72) Inventors: Heting Li, Taizhou (CN); Deqiang Wang, Taizhou (CN); Wei Chang, Taizhou (CN); Hongrui Yu, Taizhou (CN); Xiaoming Zou, Los Angeles, CA (US)

(73) Assignee: Taizhou EOC Pharma Co., Ltd., Taizhou (CN)

( * ) Notice: Subject to any disclaimer, the term of this patent is extended or adjusted under 35 U.S.C. 154(b) by 0 days.

(21) Appl. No.: 16/599,662

(22) Filed: Oct. 11, 2019

(65) Prior Publication Data
US 2020/0071336 A1 Mar. 5, 2020

Related U.S. Application Data

(63) Continuation of application No. PCT/CN2018/081660, filed on Apr. 3, 2018.

(30) Foreign Application Priority Data

Apr. 13, 2017 (CN) .................. 201710239073.X

(51) Int. Cl.
| | | |
|---|---|---|
| C07D 491/04 | (2006.01) | |
| A61P 35/04 | (2006.01) | |
| A61K 33/243 | (2019.01) | |
| A61K 31/7068 | (2006.01) | |

(52) U.S. Cl.
CPC ............ *C07D 491/04* (2013.01); *A61P 35/04* (2018.01); *A61K 31/7068* (2013.01); *A61K 33/243* (2019.01); *C07B 2200/13* (2013.01)

(58) Field of Classification Search
CPC .................................................. C07D 491/04
See application file for complete search history.

(56) References Cited

U.S. PATENT DOCUMENTS 8,304,406 B2 * 11/2012 Klein ............... A61P 11/00
514/183

FOREIGN PATENT DOCUMENTS

| CN | 1420879 A | 5/2003 |
|---|---|---|
| CN | 1769282 A | 5/2006 |
| CN | 100374435 C | 3/2008 |
| CN | 104804008 | 7/2015 |
| CN | 104804008 B | 3/2016 |
| CN | 105816855 A | 8/2016 |
| CN | 107129502 A | 9/2017 |
| WO | WO 01/23375 A2 | 4/2001 |
| WO | WO 2007/118602 A1 | 10/2007 |

OTHER PUBLICATIONS

International Search Report dated Jul. 11, 2018 in PCT Application No. PCT/CN2018/081660, filed Apr. 3, 2018 (with English Translation).
D. Strumberg, et al. "Phase I Dose Escalation Study of Telatinib (BAY 57-9352) in Patients with Advanced Solid Tumours," British Journal of Cancer, Dec. 31, 2008, pp. 1579-1585.
Strumberg, D., et al., "Phase I dose escalation study of telatinib (BAY 57-9352) in patients with advanced solid tumours , British Journal of Cancer", 99, 2008, pp. 1579-1585.
Caira, M., "Crystalline Polymorphism of Organic Compounds", Topics in Current Chemistry, vol. 198, 1998, pp. 164-208.

* cited by examiner

*Primary Examiner* — Brian E McDowell
(74) *Attorney, Agent, or Firm* — Oblon, McClelland, Maier & Neustadt, L.L.P.

(57) ABSTRACT

A crystalline form of Mod. I of Formula I:

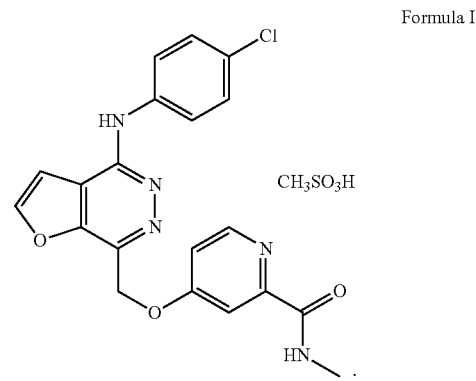

And, a process for the preparation of the crystalline form and a pharmaceutical use of the crystalline form.

16 Claims, 4 Drawing Sheets

COMPOUND OF EOC315 MOD.I CRYSTAL FORM AND PREPARATION METHOD THEREOF

CROSS-REFERENCE TO RELATED APPLICATIONS

The present application is a continuation of PCT/CN2018/081660 filed on Apr. 3, 2018, which claims the benefit of priority to CN 201710239073.X filed on Apr. 13, 2017. The disclosures of the prior applications are hereby incorporated by reference in their entirety.

TECHNICAL FIELD

The present application relates to a new crystalline form of 4-(4-chloroanilino)-7-(2-methylaminocarbonyl-4-oxymethyl) pyridylfuro[2,3-d]pyridazine mesylate (EOC315), a pharmaceutical composition comprising said crystalline form, uses of said crystalline form and pharmaceutical compositions, and methods for preparing said crystalline form.

BACKGROUND

EOC315 has a formula shown below:

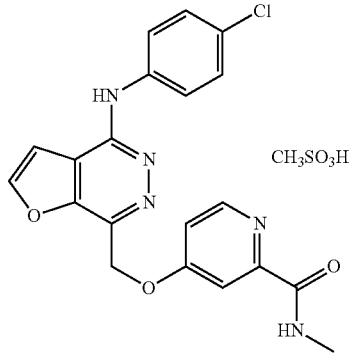

EOC315 is a potent inhibitor of the VEGFR-2 (Vascular Endothelial Growth Factor Receptor-2) tyrosine kinase, with an IC50 value of 6 nM, it also inhibits the activity of the PDGFR (Platelet-Derived Growth Factor Receptor) tyrosine kinase, with an IC50 value of 15 nM, and EOC315 is a highly selective VEGFR inhibitor.

A method for synthesizing EOC315 and analogues thereof, a pharmaceutical composition comprising EOC315, and pharmaceutical use thereof were disclosed in CN00816369 and CN200510127109. A preparation method of EOC315 for industrial production was disclosed in ZL200510140054. However, no crystalline form of EOC315 has been reported yet.

SUMMARY

The present application relates to a novel crystalline form Mod. I of EOC315, a pharmaceutical composition comprising said crystalline form, uses of said crystalline form and pharmaceutical compositions, and methods for preparing said crystalline form. The present application also relates to the use of EOC315 and/or the crystalline form thereof in combination with one or more chemotherapeutic agent for treating cancer.

The present application provides and characterizes a stable crystalline form Mod. I of EOC315. The present application also provides a method for preparing the crystalline form Mod. I of EOC315. In addition, the present application evaluates changes of X-ray powder diffraction diagrams, differential scanning calorimetry (DSC) thermogram, and crystalline structures of EOC315 before and after micronization. The present application also demonstrates that the crystalline form of EOC315 would not be changed after micronization, and is still the crystalline form Mod. I. The present application also provides a pharmaceutical composition comprising the EOC315 crystalline form Mod. I. Further, the present application provides use of the EOC315 crystalline form Mod. I in the preparation of a VEGFR-2 (Vascular Endothelial Growth Factor Receptor-2) and/or PDGFR (Platelet-Derived Growth Factor Receptor) kinase inhibitor.

The present application provides a crystalline form of 4-(4-chloroanilino)-7-(2-methylaminocarbonyl-4-oxymethyl)pyridylfuro[2,3-d]pyridazine mesylate (EOC315) of Formula I:

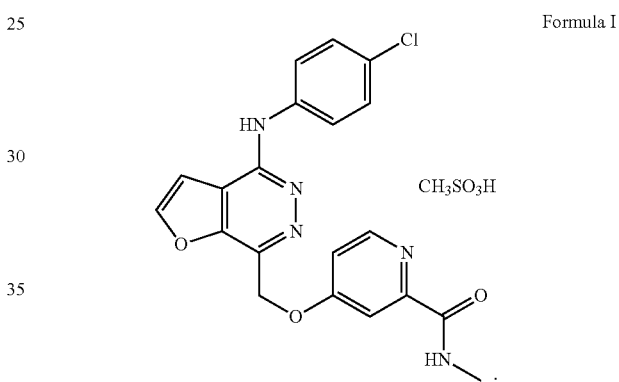

The crystalline form comprises a crystalline form Mod. I, which has an X-ray powder diffraction diagram with peaks at diffraction angles 2θ of 4.01°±0.1°, 7.85°±0.1°, 9.94°±0.1°, 13.04°±0.1°, 19.08°±0.1°, 19.46°±0.1°, 20.10°±0.1°, 21.82°±0.1°, 22.49°±0.1°, 23.76°±0.1°, 24.26°±0.1°, 27.17°±0.1°, 28.52°±0.1°, and 30.48°±0.1°. The X-ray powder diffraction diagram of the crystalline form Mod. I may be obtained with X-ray powder diffraction using CuKα radiation. The crystalline form Mod. I may have an X-ray powder diffraction diagram substantially the same as the X-ray powder diffraction diagram shown in FIG. 1.

When analyzed with an infrared spectroscopy using KBr pellet, the crystalline form Mod. I has absorption peaks at 3415 cm$^{-1}$±2 cm$^{-1}$, 3058 cm$^{-1}$±2 cm$^{-1}$, 2805 cm$^{-1}$±2 cm$^{-1}$, 1668 cm$^{-1}$±2 cm$^{-1}$, 1652 cm$^{-1}$±2 cm$^{-1}$, and 1227 cm$^{-1}$±2 cm$^{-1}$. The crystalline form Mod. I may have an infrared spectrum substantially the same as the infrared spectrum shown in FIG. 7.

The crystalline form Mod. I has a melting point of about 200.6° C. and may have a differential scanning calorimetry thermogram substantially the same as that shown in FIG. 3.

A process for preparing the crystalline form of EOC315 includes a step of crystallizing a compound of Formula I from one or more solvents of methanol, ethanol, isopropanol, butanol, hexane, heptane, acetone, ethyl propyl ether, tetrahydrofuran, toluene, ethyl acetate, and acetonitrile.

In particular, the process includes a) dissolving the compound of Formula I in the solvent to obtain a solution of the compound, and dissolving methanesulfonic acid in the solvent to obtain a methanesulfonic acid solution; b) adding the methanesulfonic acid solution to the solution of the compound; c) collecting a filter cake after filtration; and d) drying the filter cake.

A pharmaceutical composition contains the crystalline form of EOC315 and a pharmaceutically acceptable carrier or excipient. The pharmaceutical composition may be an oral solid preparation.

A method for treating cancer includes a step of administering to a subject in need thereof an effective amount of the crystalline form of EOC315. The cancer may comprise a solid tumor. The cancer may comprise an advanced solid tumor and/or a metastatic solid tumor. The cancer may be a gastric cancer (including an advanced gastric cancer) or a gastroesophageal junction cancer.

The method can further include a step of administering to the subject one or more additional chemotherapeutic agents of taxol, capecitabine, cisplatin, and gemcitabine.

In addition, the method can include a step of administering to the subject capecitabine and cisplatin.

DETAILED DESCRIPTION

The crystalline form Mod. I of EOC315 has an X-ray powder diffraction diagram with one or more peaks at a 2θ position selected from the group consisting of: 4.01° (±0.1°), 7.85° (±0.1°), 9.94° (±0.1°), 13.04° (±0.1°), 19.08° (±0.1°), 19.46° (±0.1°), 20.10° (±0.1°), 21.82° (±0.1°), 22.49° (±0.1°), 23.76° (±0.1°), 24.26° (±0.1°), 27.17° (±0.1°), 28.52° (±0.1°) and 30.48° (±0.1°). The X-ray powder diffraction diagram may be obtained by analyzing with X-ray powder diffraction using CuKα radiation.

The 2θ and d(A) of the X-ray diffraction diagram of an example of EOC315 Mod. I crystalline form are shown in table 1.

TABLE 1

2θ and d(A) values for the EOC315 Mod.
I crystalline form of the present application

| 2θ (°) | d(A) |
|---|---|
| 4.006 | 22.04 |
| 7.849 | 11.255 |
| 9.936 | 8.895 |
| 11.718 | 7.546 |
| 15.861 | 5.583 |
| 17.791 | 4.981 |
| 19.084 | 4.647 |
| 19.463 | 4.557 |
| 19.806 | 4.479 |
| 20.10 | 4.414 |
| 20.481 | 4.333 |
| 21.818 | 4.070 |
| 22.486 | 3.951 |
| 23.757 | 3.742 |
| 24.265 | 3.665 |
| 24.679 | 3.604 |
| 26.201 | 3.398 |
| 27.17 | 3.280 |
| 27.61 | 3.228 |
| 28.658 | 3.112 |
| 29.828 | 2.993 |
| 30.519 | 2.923 |
| 31.871 | 2.805 |
| 32.67 | 2.738 |
| 33.13 | 2.702 |
| 33.869 | 2.645 |
| 33.641 | 2.662 |
| 34.746 | 2.579 |
| 37.04 | 2.425 |
| 37.50 | 2.396 |
| 38.519 | 2.335 |
| 39.30 | 2.291 |
| 40.00 | 2.252 |
| 41.30 | 2.184 |
| 42.43 | 2.129 |
| 43.39 | 2.084 |
| 46.77 | 1.941 |
| 47.71 | 1.905 |
| 49.53 | 1.839 |
| 50.67 | 1.800 |
| 53.50 | 1.711 |

Figure 1:
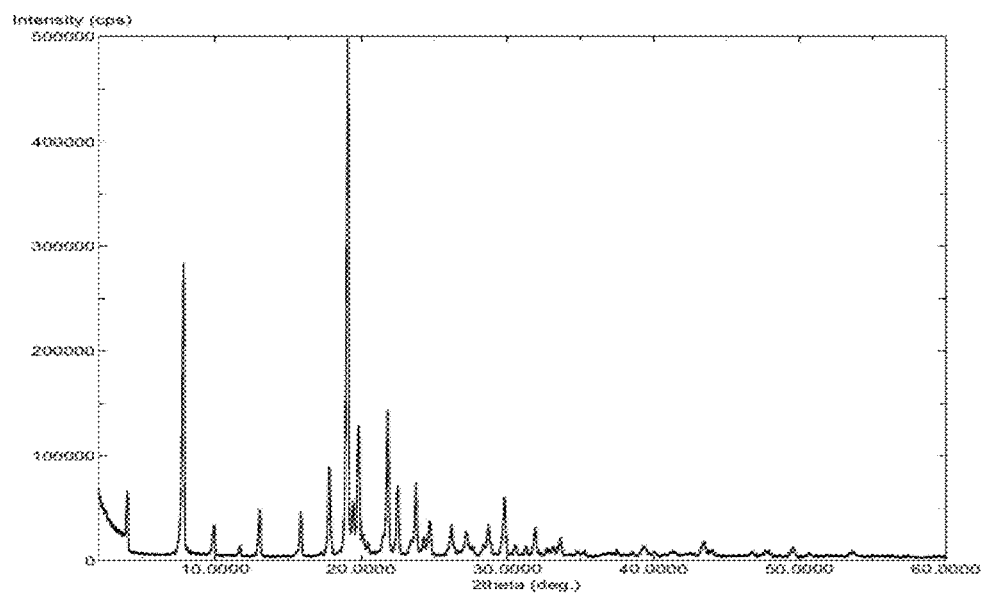
FIG. 1 shows an X-ray powder diffraction diagram of an EOC315 crystalline form Mod. I.

An example of the X-ray diffraction diagram of the EOC315 Mod. I crystalline form analyzed using X-ray diffraction (CuKα) is shown in FIG. 1.

In some embodiments, the crystalline form Mod. I of the present application has an X-ray powder diffraction diagram substantially the same as the X-ray powder diffraction diagram shown in FIG. 1, when analyzed with the X-ray powder diffraction (CuKα).

Figure 3:
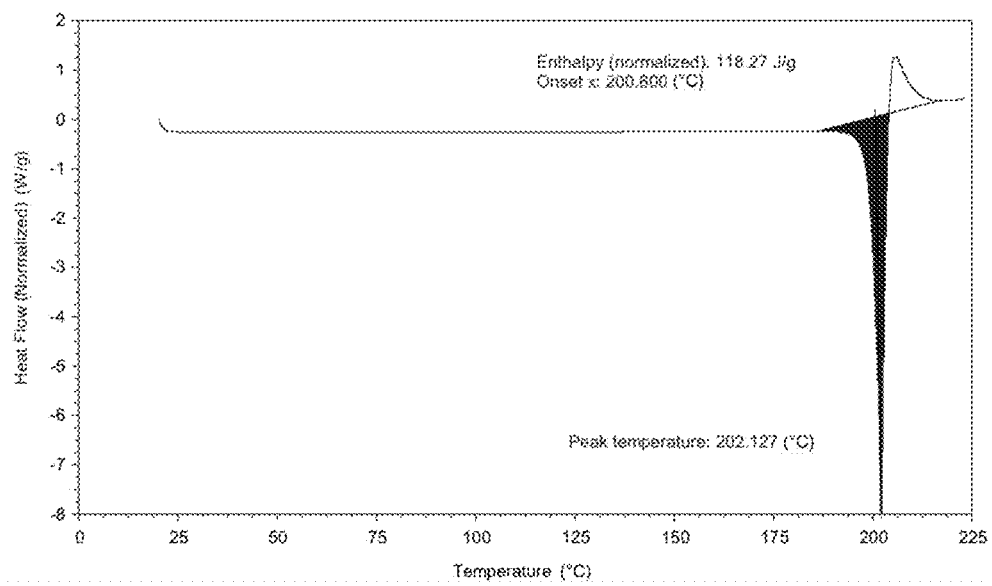
FIG. 3 shows a differential scanning calorimetry (DSC) graph of the EOC315 crystalline form Mod. I.
Figure 8:
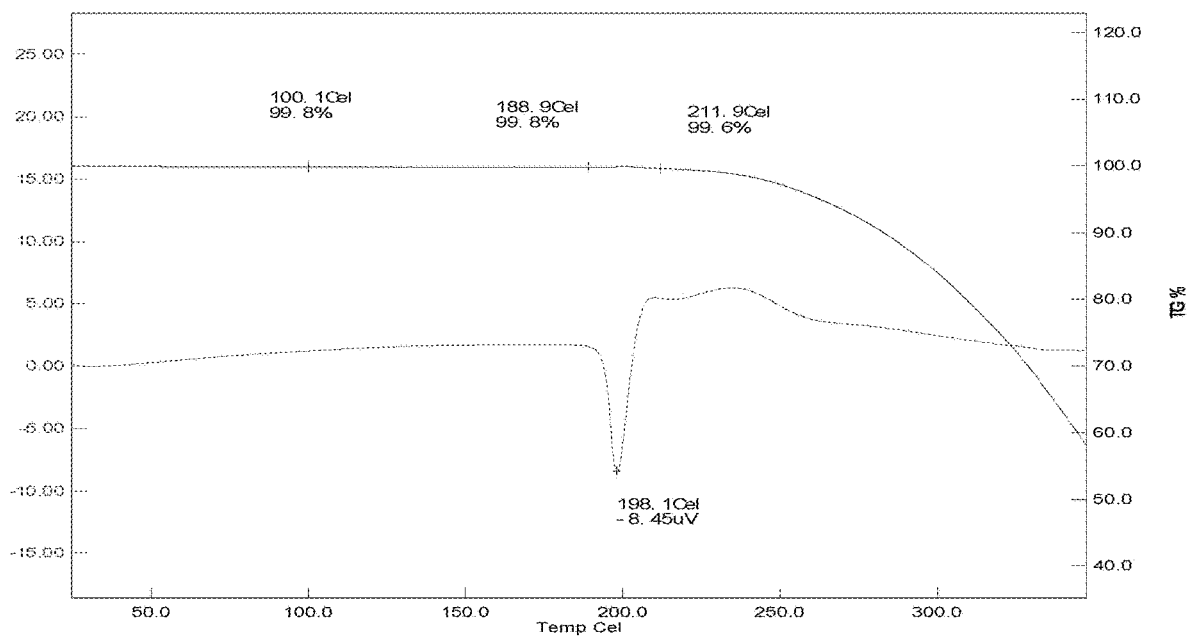
FIG. 8 shows a thermogravimetric analysis (TG/DTA) graph of the EOC315 crystalline form Mod. I.

The EOC315 Mod. I crystalline form may have a melting point of about 200.6° C. and its DSC thermoanalysis result is shown in FIG. 3. Thermogravimetric analysis (TGA) shows that the Mod. I crystalline form has a degradation temperature of about 241.71° C. and its TGA graph is shown in FIG. 8.

In some embodiments, the crystalline form Mod. I of the present application has a differential scanning calorimetry thermogram that is substantially the same as that shown in FIG. 3.

In some embodiments, the crystalline form Mod. I of the present application has a degradation temperature of about 241.71° C., as shown, for example, in thermogravimetric analysis.

In some embodiments, the crystalline form Mod. I of the present application has a TGA graph substantially the same as that shown in FIG. 8.

Figure 7:
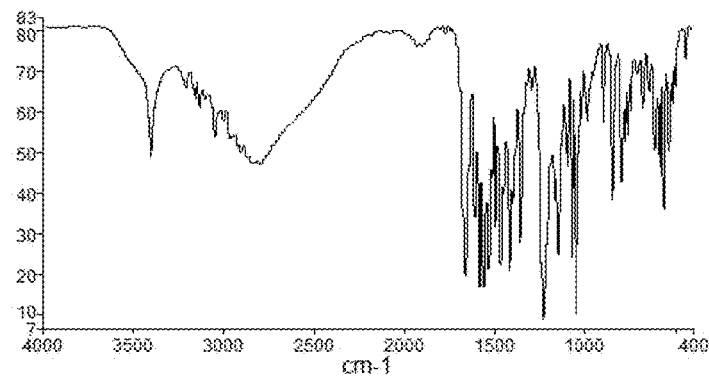
FIG. 7 shows an infrared (IR) spectrum of the EOC315 crystalline form Mod. I.

The infrared spectrum (KBr) of an example of the EOC315 Mod. I crystalline form shows absorption peaks at 3415 cm$^{-1}$, 3058 cm$^{-1}$, 2805 cm$^{-1}$, 1668 cm$^{-1}$, 1652 cm$^{-1}$, and 1227 cm$^{-1}$. The infrared detection result of the example is shown in FIG. 7.

Accordingly, in some embodiments, the crystalline form Mod. I of the present application has absorption peaks at 3415 cm$^{-1}$ (±2 cm$^{-1}$), 3058 cm$^{-1}$ (±2 cm$^{-1}$), 2805 cm$^{-1}$ (±2 cm$^{-1}$), 1668 cm$^{-1}$ (±2 cm$^{-1}$), 1652 cm$^{-1}$ (±2 cm$^{-1}$) and 1227 cm$^{-1}$ (±2 cm$^{-1}$), when analyzed with an infrared spectroscopy (KBr).

In some embodiments, the crystalline form Mod. I of the present application has an infrared spectrum substantially the same as the infrared spectrum shown in FIG. 7.

Figure 5:
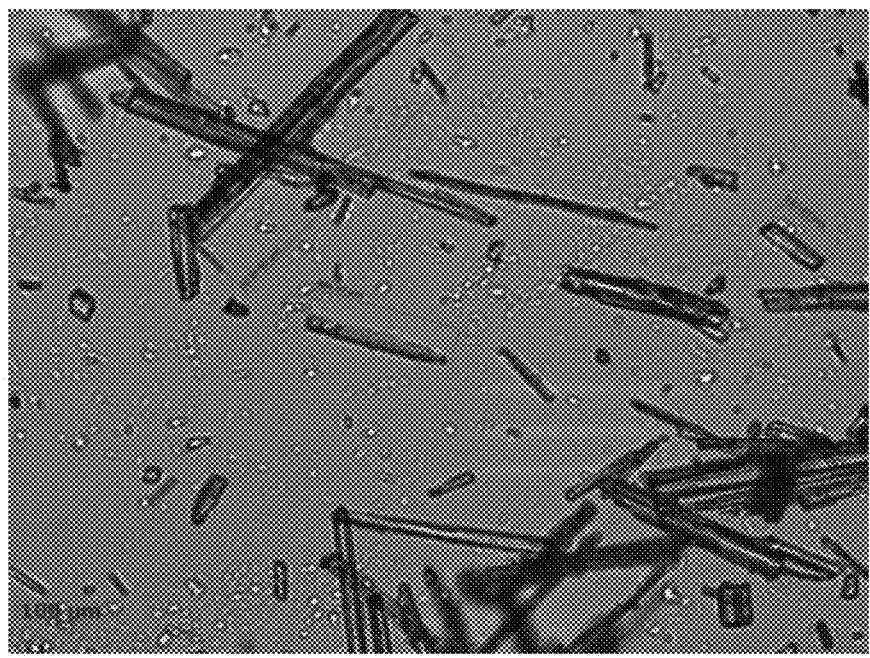
FIG. 5 shows a hot-stage polarized optical microscope (HSM) image of the EOC315 crystalline form Mod. I.

The result of hot-stage polarized optical microscope (HSM) analysis of the Mod. I crystalline form shows that the product has an acicular crystal having a relatively large particle length, which may be up to hundreds of microns, and has a high crystallinity. The HSM image is shown in FIG. 5.

In another aspect, the present application provides a process for the preparation of EOC315 Mod. I crystalline form. The method may comprise crystallizing a compound of Formula I (EOC315) from a solvent. The solvent may be selected from the group consisting of methanol, ethanol, isopropanol, butanol, hexane, heptane, acetone, ethyl propyl ether, tetrahydrofuran, toluene, ethyl acetate, acetonitrile, and a mixture thereof.

In some embodiments, the solvent is selected from the group consisting of methanol, ethanol, isopropanol, butanol, and a mixture thereof.

For example, the process may comprise the following steps: 1) dissolving EOC315 in the solvent of the present application to obtain an EOC315 solution, and dissolving methanesulfonic acid in the solvent to obtain a methanesulfonic acid solution; 2) adding the methanesulfonic acid solution to the EOC315 solution; 3) collecting a filter cake after filtration; and 4) drying the filter cake.

Prior to filtration, the process may further comprise removing at least a portion (e.g., a majority) of the solvent through vacuum distillation, then adding a polar or non-polar solvent, thereafter reslurring the solution, e.g., at 0-30° C.

In some embodiments, the process of the present application comprises: dissolving a free alkali of EOC315 in an organic solvent, and adding methanesulfonic acid in an organic solution dropwise; then distilling a portion of the solvent; and obtaining the EOC315 crystalline form Mod. I after adding another solvent for crystallization with decreasing temperature.

An exemplified detailed method for preparing the Mod. I crystalline form of EOC315 may comprise the following steps:

1) dissolving a free alkali of EOC315 in a solvent to obtain an EOC315 solution, and dissolving methanesulfonic acid in a solvent to obtain a methanesulfonic acid solution;

2) adding the methanesulfonic acid solution to the EOC315 solution at 20-90° C.;

3) removing most of the solvent through vacuum distillation, and adding a polar or non-polar solvent, and reslurring the solution at 0-30° C., and collecting a filter cake after filtration;

4) vacuum drying the collected filter cake at 25-90° C.

The solvent in step 1) may be a single organic solvent selected from methanol, ethanol, isopropanol, butanol, hexane, heptane, acetone, ethyl propyl ether, tetrahydrofuran, toluene, ethyl acetate and acetonitrile, or a mixture thereof.

In some embodiments, the solvent in step 1) is a single solvent selected from methanol, ethanol, isopropanol and butanol, or a mixture thereof.

Particle size of a drug may affect the solubility of the drug (particularly for oral solid preparations) in various solvents, thereby may affect the bioavailability of the drug in human bodies, which may then affect the efficacy of the drug.

In another aspect, the present application provides a micropowder of the EOC Mod. I crystalline form. The micropowder may be obtained by micronizing the EOC Mod. I crystalline form.

In some embodiments, the dried EOC315 crystalline form Mod. I may be micronized to obtain the EOC315 crystalline form Mod. I micropowder, with a particle size D90≤15 μm.

When analyzed with X-ray powder diffraction (CuKα), the EOC315 crystalline form Mod. I micropowder has an X-ray diffraction diagram substantially the same as that shown in FIG. 2, and is substantially consistent with the diagram prior to micronization, indicating that the crystalline form of the sample does not change after micronization.

However, some changes of the solid properties, for example, the size and preferred orientation of particles may affect the relative intensities of the peaks in the diagram, but do not affect the positions of the peaks, especially the positions of peaks with low 2θ values. The diagram obtained after micronization also shows a certain degree of base line upheaval, which may indicate changes of crystallinity.

The 2θ and d(A) of the X-ray diffraction diagram obtained after micronization of an example of EOC315 Mod. I crystalline form are shown in table 2.

TABLE 2

2θ and d(A) values of the micronized EOC315 crystalline form Mod. I

| 2θ (°) | d(A) |
| --- | --- |
| 3.898 | 22.65 |
| 7.766 | 11.375 |
| 9.856 | 8.967 |
| 12.953 | 6.829 |
| 15.777 | 5.613 |
| 17.798 | 4.979 |
| 18.998 | 4.667 |
| 19.357 | 4.582 |
| 19.734 | 4.475 |
| 20.039 | 4.427 |
| 21.423 | 4.144 |
| 21.742 | 4.084 |
| 22.394 | 3.967 |
| 23.27 | 3.820 |
| 23.413 | 3.796 |
| 23.616 | 3.764 |
| 24.23 | 3.670 |
| 24.521 | 3.627 |
| 26.09 | 3.413 |
| 27.07 | 3.291 |
| 27.534 | 3.237 |
| 28.608 | 3.118 |
| 29.715 | 3.004 |
| 30.480 | 2.930 |
| 31.80 | 2.812 |
| 32.66 | 2.740 |
| 33.05 | 2.708 |
| 33.869 | 2.645 |
| 35.209 | 2.547 |
| 36.74 | 2.444 |
| 39.38 | 2.286 |
| 39.92 | 2.256 |
| 41.11 | 2.194 |
| 41.46 | 2.176 |
| 41.91 | 2.154 |
| 43.34 | 2.086 |

TABLE 2-continued

2θ and d(A) values of the micronized
EOC315 crystalline form Mod. I

| 2θ (°) | d(A) |
|---|---|
| 46.708 | 1.943 |
| 47.838 | 1.899 |
| 50.61 | 1.802 |

Figure 4:
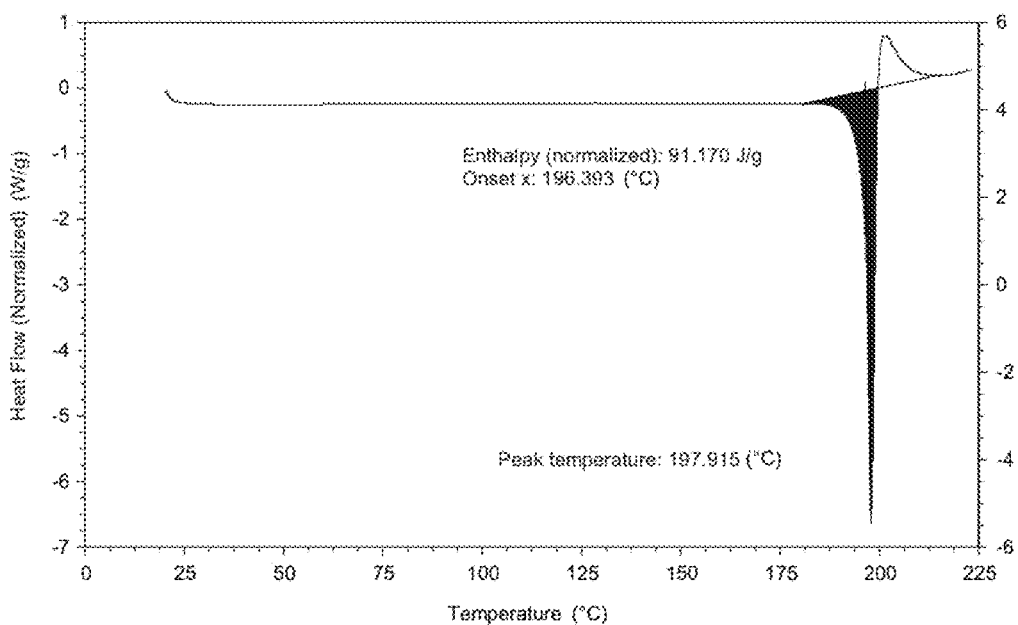
FIG. 4 shows a differential scanning calorimetry (DSC) graph of the micronized EOC315 crystalline form Mod. I.

The EOC315 crystalline form Mod. I micropowder has a transition temperature of 196.39° C., which is lower than 200.6° C. (the transition temperature of the crystalline form of EOC315 before the micronization), indicating that the micronized crystalline form may have a lower crystallinity, and the DSC thermoanalysis result of the micronized crystal is shown in FIG. 4.

Figure 6:
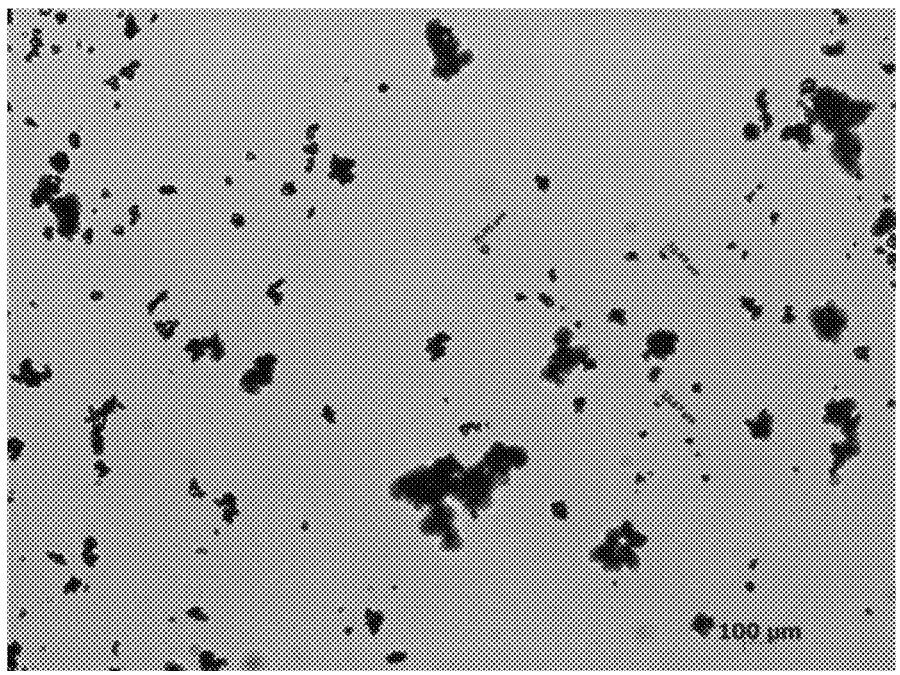
FIG. 6 shows a hot-stage polarized optical microscope (HSM) image of the micronized EOC315 crystalline form Mod. I.

Result of the hot-stage polarized optical microscope (HSM) analysis of the EOC315 crystalline form Mod. I micropowder shows that the sample is micropowder crystals (less than 10 microns) and has a lower crystallinity, and the HSM analysis result is shown in FIG. 6.

According to the HSM analysis result, X-ray powder diffraction result, and DSC result, EOC315 crystalline form Mod. I micropowder is of the crystalline form Mod. I.

The crystalline form of the EOC315 crystalline form Mod. I micropowder remains unchanged as compared with that of the compound before micronization, and both are the Mod. I crystalline form except that the compound before micronization has a larger particle size and a higher purity.

In another aspect, the present application further provides a pharmaceutical composition, comprising said EOC315 crystalline form Mod. I of the present application and one or more pharmaceutically acceptable carriers or excipients. The EOC315 crystalline form Mod. I of the present application and the one or more pharmaceutically acceptable carriers or excipients may be formulated into a common dosage form in the pharmaceutical field, such as a tablet, a capsule, an injection, etc., and preferably an oral solid preparation.

The EOC315 crystalline form Mod. I and the one or more solid carriers may be mixed to prepare an orally-administered pharmaceutical composition. The mixture may be granulated and the obtained granules may be mixed, when desired. Tablets or tablet cores may be obtained by adding an additional excipient, when desired or necessary. In particular, suitable carriers are filler (such as sugar (e.g., lactose, saccharose, mannitol, and sorbitol), cellulose preparation, and/or calcium phosphate (e.g., tricalcium phosphate and calcium hydrogen phosphate)), binder (such as starch (e.g., corn starch, wheat starch, rice starch, and potato starch), methylcellulose, hydroxypropyl methylcellulose, sodium carboxymethylcellulose, and/or polyvinylpyrrolidone), and/or, if needed, disintegrator (such as the aforementioned starch, carboxymethyl starch, cross-linked polyvinylpyrrolidone, alginic acid or salt thereof (e.g., sodium alginate)). In particular, additional excipients may be fluidity regulator and lubricant, such as silicic acid, talcum, stearic acid of a salt thereof (e.g., magnesium stearate or calcium stearate), and/or polyethylene glycol or a derivative thereof.

The tablet core may have an appropriate coating, and the coating is conducted by particularly using a concentrated sugar solution which can contain Arabic gum, talcum, polyvinylpyrrolidone, polyethylene glycol and/or titanium dioxide, or conducted in a coating solution in a suitable organic solvent or solvent mixture. Dye or pigment may be added into the tablet or the tablet coating, for example, for identifying or demonstrating the different doses of EOC315.

In another aspect, the present application provides the EOC315 crystalline form Mod. I as a potent VEGFR-2 (Vascular Endothelial Growth Factor Receptor-2) and PDGFR (Platelet-Derived Growth Factor Receptor) kinase inhibitor, which can effectively inhibit the growth of relevant tumor cells.

In some embodiments, the present application provides use of the EOC315 crystalline form Mod. I in the preparation of a VEGFR-2 and/or PDGFR inhibitor.

EOC315 or the EOC 315 Mod. I crystalline form may be used in combination with a chemotherapeutic drug, such as taxol (Taxol®), capecitabine (Xeloda®) and gemcitabine (Gemzar®).

Such a combination may: 1) produce better efficacy in decreasing the growth of a tumor or even eliminating the tumor compared with the delivery of any single agent aforementioned; 2) provide lower dosage of the chemotherapeutic agent administered; 3) provide a chemotherapeutic method that may be well-tolerated by a patient and has less observed harmful pharmacological complications than a mono-chemotherapy and other certain combination therapies; 4) provide a broader therapeutic spectrum for a different type of cancer in mammals, and particularly in human beings; 5) provide a higher speed of response for patients under treatment; 6) provide a longer survival time for the patients under treatment compared with standard chemotherapies; and/or 7) provide a longer tumor progression time compared with other anticancer agents used in combination, which has caused antagonism, and/or produce at least the same efficacy and tolerance as the agent used alone.

EOC315 or the EOC 315 Mod. I crystalline form can be simultaneously, separately, or consecutively delivered in a pharmaceutically effective amount with one or more of the cytotoxic agents. The dose of the administered combined active agents ("pharmaceutically effective amount") varies in a broad range, depending on the disease to-be-treated and the ways of delivery. The dose may comprise any amount that is effective to achieve an expected treatment. It is within the abilities of those skilled in the art to determine the "pharmaceutically effective amount" of the combined active agents.

In another aspect, the present application provides a method for alleviating and/or treating cancer. The method may comprise administering to a subject in need thereof an effective amount of the EOC 315 Mod. I crystalline form of the present application. In some embodiments, the method may further comprise administering to said subject one or more additional chemotherapeutic agent.

In another aspect, the present application provides a method for alleviating and/or treating cancer. The method may comprise administering to a subject in need thereof an effective amount of EOC 315 in combination with one or more additional chemotherapeutic agent.

The cancer may comprise a solid tumor. The cancer may comprise an advanced solid tumor and/or a metastatic solid tumor, such as a metastatic advanced solid tumor. For example, the cancer may be selected from the group consisting of a gastric cancer and a gastroesophageal junction (GEJ) cancer. The gastric cancer may be an advanced gastric cancer, such as an advanced metastatic gastric cancer. The gastroesophageal junction (GEJ) cancer may be an advanced gastroesophageal junction (GEJ) cancer.

The one or more additional chemotherapeutic agent may be selected from the group consisting of taxol, capecitabine, cisplatin and gemcitabine. In some embodiments, the one or more additional chemotherapeutic agent comprises capecitabine and cisplatin.

In some embodiments, the present application provides a method for alleviating and/or treating cancer. The method may comprise administering to a subject in need thereof an effective amount of EOC 315 and/or EOC315 Mod. I crystalline form in combination with capecitabine and cisplatin.

In the method of the present application, the capecitabine, the EOC 315 and/or EOC315 Mod. I crystalline form may be administered after cisplatinum administration.

EXAMPLES

The present application can be further described with the following examples. However, the present application is not limited to the following examples, and these examples do not limit the scope of the present application in any way. Certain changes and adjustments made by those skilled in the art within the scope of the claims shall be considered to fall within the scope of the present application.

Example 1

Preparation of EOC315 Crystalline Form Mod. I

The reparation process of an EOC315 crystalline form Mod. I comprised the following steps:
1) 9 g EOC315 alkali was dissolved in 90 mL methanol to obtain an EOC315 solution, and 2.5 g methanesulfonic acid was dissolved in 16 mL methanol to obtain a methanesulfonic acid solution;
2) the methanesulfonic acid solution was added dropwise to the EOC315 solution at 50° C., and then was heated for 15 min;
3) a portion of the solvent was removed through the vacuum distillation conducted on the filtrate, then 200 ml isopropanol was added and vacuum distillation was continued until the solution volume was about 250 mL, then the solution was subjected to cooling crystallization for 1 hr, and the liquid was sucked away to collect the filter cake;
4) the collected filter cake was dried under vacuum at 45° C. to obtain EOC315 crystalline form Mod. I, with a yield of 90.5~96.3% and a purity of 99.1~99.9%.

The X-ray powder diffraction diagram as shown in FIG. 1 was obtained from the X-ray diffraction analysis.

Example 2

Analysis of the EOC315 Crystalline Form Mod. I of Example 1 by Differential Scanning Calorimetry (DSC)

The DSC trace was recorded in an aluminum dish at the heating speed of 10° C./min in a nitrogen atmosphere, and it was determined that there appeared a sharp endothermic peak at 200.7° C. for the EOC315 obtained in example 1, indicating that EOC315 was in a single Mod. I crystalline form with a melting point of 200.7° C. The analysis result is shown in FIG. 3.

As known by those of ordinary skill in the art, the determined melting temperature depends on the experimental conditions, and particularly on the heating speed adopted. In addition, the melting temperature would be influenced by the product purity. The reported melting temperature was determined by using the product with a purity of at least 98.5%.

Example 3

Analysis of the EOC315 Crystalline Form Mod. I of Example 1 by X-Ray Powder Diffraction Germanium-monochromatized CuKα1—radiation was used to record the X-ray powder diffraction data at room temperature. A small linear position-sensitive detector was used to carry out the 2θ scanning within a range of 3°≤2θ≤35° (step length: 0.5°) with an angular resolution of 0.08° at room temperature. The X-ray powder diffraction diagram is shown in FIG. 1, wherein the values of 2θ and d(A) are shown in table 1.

Those of ordinary skill in the art will appreciate that there may be a measurement deviation in the obtained X-ray diffraction diagram, depending on the measurement conditions. In particular, it is generally known that the intensity of an X-ray diffraction diagram may fluctuate according to the crystal habit of a substance and the adopted measurement conditions. In addition, the measurement deviation of a diffraction angle θ of a conventional X-ray diffraction diagram is usually about ±0.1° at a given temperature, and moreover, such degree of measurement deviation shall be taken into consideration when the diffraction angle is involved. Therefore, any crystalline form with an X-ray diffraction diagram substantially consistent with the X-ray powder diffraction diagram disclosed in the figures of the present application shall fall within the scope of the present application.

Example 4

Thermogravimetric Analysis (TG/DTA) of the EOC315 Crystalline Form Mod. I of Example 1

Under a nitrogen atmosphere and at a heating speed of 10° C./min, it was measured that EOC315 obtained in example 1 had a mass fraction of 99.8% at 188.9° C., with a weight loss of 0.2%, nearly no weight loss, and this indicated that there was no crystallization solvent and a low content of volatile substances in the sample. The DTA curve of a test sample has an endothermic peak at 198.1° C., which is consistent with the DSC result. The TGA graph is shown in FIG. 8.

As known by those of ordinary skill in the art, the measured temperature depends on the experimental conditions, and particularly on the heating speed adopted. In addition, the temperature would be influenced by the product purity. The reported melting temperature was determined by using the batch of product with a purity of at least 98.5%.

Example 5

Hot-Stage Polarized Optical Microscope (HSM) Analysis of the EOC315 Crystalline Form Mod. I The result of HSM analysis on an EOC315 sample showed that this sample was an acicular crystal with large granularity (with lengths up to hundreds of microns), and the crystallinity was high. The HSM image is shown in FIG. 5.

Example 6

Infrared Analysis of the EOC315 Crystalline Form Mod. I of Example 1

Diffuse reflection (KBr) was used to record the infrared spectrum of the EOC315 Mod. I crystal. The infrared spectrum is shown in FIG. 7, and the main infrared bands and assignments thereof are shown in table 3.

TABLE 3

Main absorption peaks in the infrared spectrum of the EOC315 Mod. I crystal and assignments thereof

| Sample No. | Absorption peaks of test samples (cm$^{-1}$) | Vibration type | Group (assignment) | Intensities of absorption peaks |
|---|---|---|---|---|
| 1 | 3414.66 | $v_{N-H}$ | N—H stretching vibration | m |
| 2 | 3057.73 | $v_{C-H}$ | C—H stretching vibration in aromatic ring | m |
| 3 | 2804.69 | $v_{C-H}$ | Saturated C—H stretching vibration | m |
| 4 | 1668.18 | $v_{C=O}$ | C=O stretching vibration | vs |
| 5 | 1652.40, 1608.18, 1584.45, 1557.03, 1531.35, 1492.12 | $v_{C-C}$, $v_{C-N}$ | Skeleton stretching vibration of aromatic ring | m~s |
| 6 | 1227.16, 1142.23, 1067.69, 1040.92 | $v_{C-O}$, $v_{C-N}$ | C—O and C—N stretching vibrations | vs |

As known by those of ordinary skill in the art, the acceptable wavenumber shift tolerance is ±2 cm$^{-1}$ based on the adopted instruments and measurement conditions. Therefore, any solid-state form with an FT-Raman spectrum substantially consistent with the FT-Raman spectrum disclosed in the figures of the present application may fall within the scope of the present application.

Example 7

Micronization of the EOC315 Crystalline Form Mod. I Obtained in Example 1

Figure 2:
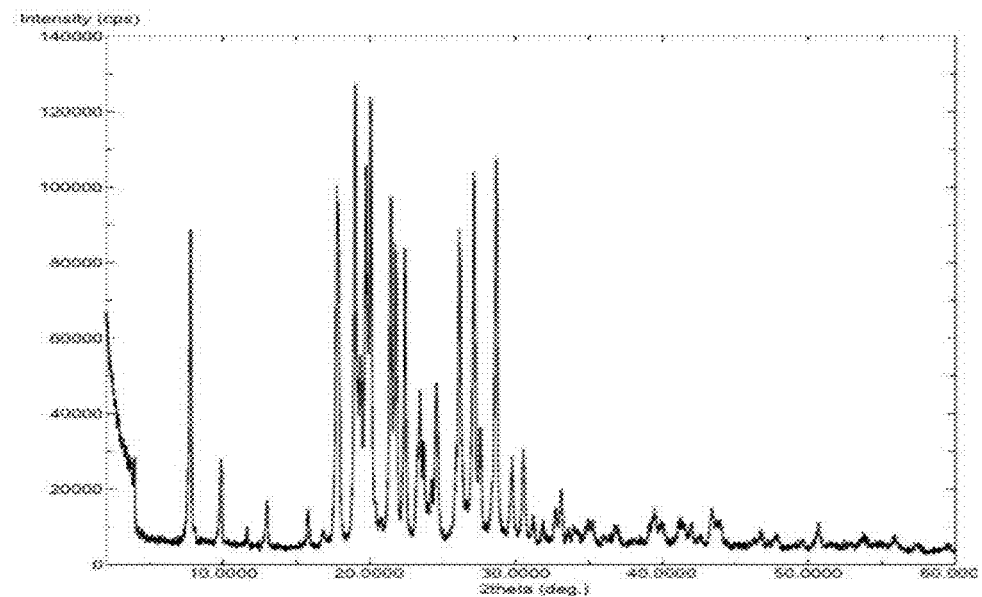
FIG. 2 shows an X-ray diffraction diagram of the micronized EOC315 crystalline form Mod. I.

The pressure of the micronization equipment was set to be ≥0.65 MPa to obtain an EOC315 crystalline form micropowder, with a particle size D90≤15 μm. The X-ray powder diffraction, DSC, and HSM data of the micronized sample were measured using the aforementioned methods, and the results are shown in FIG. 2, FIG. 4, and FIG. 6.

It can be concluded from the figures that the crystalline form of the micronized EOC315 remained unchanged, and was still the crystalline form Mod. I.

Example 8

Inhibitory Effect of the EOC315 Crystalline Form Mod. I on Tumor Cells

The EOC315 crystalline form Mod. I shows biochemical and cellular activity in vitro, and is consistent with the anti-angiogenesis action mechanism. Therefore, a study was conducted in a Colo-205 human CRC xenograft model to evaluate whether the anti-tumor activity observed in vivo is consistent with the hypothesis. The microvessel density of a tumor was determined by the quantitative histomorphometry after the endothelial cell marker CD31 was stained. Four hours after the first drug delivery, the declining level of the tumor MVA was further increased compared with each solvent control group (32%; P<0.05). Twenty-four hours after the administration, the declining level of the tumor MVA was further increased (53%; P<0.01). The effect was more obvious 3 days after the administration, and moreover, MVA was observed to decrease by 64% and 68% at 4 hours and 6 hours, respectively.

Those skilled in the art may discover from the aforementioned experimental results that the growth of tumor cells was significantly suppressed when an EOC315 crystalline form Mod. I was used.

Example 9

Study on the Efficacy of EOC315 Used in Combination with Capecitabine (X) and Cisplatinum (P) in Patients with Advanced Gastric Cancers or Gastroesophageal Junction (GEJ) Cancers After at most 6 cycles of cisplatinum treatment, both or either of capecitabine and EOC315 was delivered to a subject in a dosage previously used according to the toxic reaction conditions, until the disease progressed.

Forty-eight subjects in total were enrolled for this study. Forty-five subjects (94%) had tumor metastasis and thirty-five subjects (73%) had more than two metastatic sites thereinto. The livers of 26 subjects (54%) were involved due to the tumors. The major sites involved for the 26 subjects (54%) were gastroesophageal junctions, the major sites involved for 22 subjects (46%) were stomach, and the majority of the subjects got an ECOG score of 1 (n=41, 85%).

Thirty-nine subjects completed at least one course of treatment and got therapeutic effect evaluation. The objective response rate (ORR) was 67%. One subject (2.6%) achieved the complete response. Twenty-five subjects (64.1%) achieved the partial response. Eleven subjects (28.2%) showed a stable condition and maintained such a condition for more than 12 weeks. It was evaluated that the objective response generally occurred in the previous two cycles of treatment and lasted for a long time, which was related closely to the duration of treatment received by the subjects. The anti-tumor effect was not related to tumor tissue type, the primary site, whether or not liver is involved, or the study center. Median progression-free survival (PFS) was 4.5 months. Kaplan-Meier analysis showed that the proportion of patients without tumor-progression within 6 months was 52%. The median time to progression for patients showing tumor remission was 6.4 months. Median overall survival (OS) was estimated to be 7.8 months, and the 1-year survival rate was 33%.

The preliminary result showed a high overall response rate (67% of objective response rate (ORR), which was almost twice the historical response rate achieved by chemotherapy alone) and a long response time, and there was evidence showing a prolonged survival.

Example 10

Result of the Stability Experiment

Long-term stability over twelve months was evaluated at 25° C. and a relative humidity of 60%; or accelerated stability over six months was evaluated at 40° C. and a relative humidity of 75%. The results are shown in table 4 and 5 below:

TABLE 4

The long-term stability study of EOC315 (temperature: 25° C. ± 2° C.; relative humidity (RH): 60% ± 5%)

| Item evaluated | Limit requirement | | Batch No. | Month 0 | | Month 3 | | Month 6 | |
|---|---|---|---|---|---|---|---|---|---|
| Related substance | Impurity 1 | 0.17% | 151211 | Impurity 1 | Undetected | Impurity 1 | Undetected | Impurity 1 | Undetected |
| | Impurity 2 | 0.17% | | Impurity 2 | Undetected | Impurity 2 | Undetected | Impurity 2 | 0.0028% |
| | Impurity 3 | 0.17% | | Impurity 3 | 0.016% | Impurity 3 | Undetected | Impurity 3 | 0.099% |
| | Impurity 4 | 3.0% | | Impurity 4 | 0.36% | Impurity 4 | 0.4% | Impurity 4 | 0.42% |
| | Impurity 5 | 0.10% | | Impurity 5 | 0.02% | Impurity 5 | 0.01% | Impurity 5 | Undetected |
| | Impurity 6 | 0.10% | | Impurity 6 | 0.01% | Impurity 6 | Undetected | Impurity 6 | 0.01% |
| | Maximum single impurity | 0.15% | | Maximum single impurity | 0.0079% | Maximum single impurity | Undetected | Maximum single impurity | 0.013% |
| | Total impurity | 1.0% | | Total impurity | 0.53% | Total impurity | 0.5% | Total impurity | 0.73% |
| | | | 151212 | Impurity 1 | Undetected | Impurity 1 | Undetected | Impurity 1 | Undetected |
| | | | | Impurity 2 | Undetected | Impurity 2 | Undetected | Impurity 2 | Undetected |
| | | | | Impurity 3 | 0.011% | Impurity 3 | Undetected | Impurity 3 | 0.031% |
| | | | | Impurity 4 | 0.46% | Impurity 4 | 0.5% | Impurity 4 | 0.54% |
| | | | | Impurity 5 | 0.01% | Impurity 5 | 0.02% | Impurity 5 | 0.02% |
| | | | | Impurity 6 | Undetected | Impurity 6 | Undetected | Impurity 6 | 0.01% |
| | | | | Maximum single impurity | 0.012% | Maximum single impurity | Undetected | Maximum single impurity | 0.070% |
| | | | | Total impurity | 0.65% | Total impurity | 0.6% | Total impurity | 0.88% |
| | | | 151213 | Impurity 1 | Undetected | Impurity 1 | Undetected | Impurity 1 | Undetected |
| | | | | Impurity 2 | Undetected | Impurity 2 | Undetected | Impurity 2 | Undetected |
| | | | | Impurity 3 | 0.011% | Impurity 3 | Undetected | Impurity 3 | 0.033% |
| | | | | Impurity 4 | 0.35% | Impurity 4 | 0.38% | Impurity 4 | 0.40% |
| | | | | Impurity 5 | Undetected | Impurity 5 | 0.01% | Impurity 5 | Undetected |
| | | | | Impurity 6 | Undetected | Impurity 6 | Undetected | Impurity 6 | 0.01% |
| | | | | Maximum single impurity | 0.0085% | Maximum single impurity | Undetected | Maximum single impurity | 0.016% |
| | | | | Total impurity | 0.52% | Total impurity | 0.5% | Total impurity | 0.63% |
| Crystalline form | ModI | | 151211 | ModI | | / | | ModI | |
| | | | 151212 | ModI | | / | | ModI | |
| | | | 151213 | ModI | | / | | ModI | |

| | Item evaluated | Limit requirement | | Batch No. | Month 9 | | Month 12 | |
|---|---|---|---|---|---|---|---|---|
| | Related substance | Impurity 1 | 0.17% | 151211 | Impurity 1 | Undetected | Impurity 1 | Undetected |
| | | Impurity 2 | 0.17% | | Impurity 2 | Undetected | Impurity 2 | Undetected |
| | | Impurity 3 | 0.17% | | Impurity 3 | Undetected | Impurity 3 | Undetected |
| | | Impurity 4 | 3.0% | | Impurity 4 | 0.43% | Impurity 4 | 0.46% |
| | | Impurity 5 | 0.10% | | Impurity 5 | 0.02% | Impurity 5 | 0.01% |
| | | Impurity 6 | 0.10% | | Impurity 6 | Undetected | Impurity 6 | 0.03% |
| | | Maximum single impurity | 0.15% | | Maximum single impurity | 0.013% | Maximum single impurity | Undetected |
| | | Total impurity | 1.0% | | Total impurity | 0.61% | Total impurity | 0.63% |
| | | | | 151212 | Impurity 1 | Undetected | Impurity 1 | Undetected |
| | | | | | Impurity 2 | Undetected | Impurity 2 | Undetected |
| | | | | | Impurity 3 | Undetected | Impurity 3 | Undetected |
| | | | | | Impurity 4 | 0.56% | Impurity 4 | 0.58% |
| | | | | | Impurity 5 | 0.01% | Impurity 5 | Undetected |
| | | | | | Impurity 6 | 0.01% | Impurity 6 | 0.02% |
| | | | | | Maximum single impurity | Undetected | Maximum single impurity | Undetected |
| | | | | | Total impurity | 0.77% | Total impurity | 0.80% |
| | | | | 151213 | Impurity 1 | Undetected | Impurity 1 | Undetected |
| | | | | | Impurity 2 | Undetected | Impurity 2 | Undetected |
| | | | | | Impurity 3 | Undetected | Impurity 3 | Undetected |
| | | | | | Impurity 4 | 0.42% | Impurity 4 | 0.42% |
| | | | | | Impurity 5 | Undetected | Impurity 5 | 0.01% |
| | | | | | Impurity 6 | Undetected | Impurity 6 | Undetected |
| | | | | | Maximum single impurity | Undetected | Maximum single impurity | Undetected |
| | | | | | Total impurity | 0.58% | Total impurity | 0.58% |
| | Crystalline form | ModI | | 151211 | / | | ModI | |
| | | | | 151212 | / | | ModI | |
| | | | | 151213 | / | | ModI | |

TABLE 5

The stability evaluation of EOC315 under an accelerated condition (temperature: 40° C. ± 2° C.; relative humidity (RH): 75% ± 5%)

| Study item | Limit requirement | | Batch No. | Month 0 | | Month 1 | | Month 2 | |
|---|---|---|---|---|---|---|---|---|---|
| Related substance | Impurity 1 | 0.17% | 151211 | Impurity 1 | Undetected | Impurity 1 | Undetected | Impurity 1 | Undetected |
| | Impurity 2 | 0.17% | | Impurity 2 | Undetected | Impurity 2 | 0.0031% | Impurity 2 | Undetected |
| | Impurity 3 | 0.17% | | Impurity 3 | 0.016% | Impurity 3 | 0.0040% | Impurity 3 | 0.0013% |
| | Impurity 4 | 3.0% | | Impurity 4 | 0.36% | Impurity 4 | 0.4% | Impurity 4 | 0.4% |
| | Impurity 5 | 0.10% | | Impurity 5 | 0.02% | Impurity 5 | Undetected | Impurity 5 | Undetected |
| | Impurity 6 | 0.10% | | Impurity 6 | 0.01% | Impurity 6 | 0.01% | Impurity 6 | 0.01% |
| | Maximum single impurity | 0.15% | | Maximum single impurity | 0.0079% | Maximum single impurity | 0.011% | Maximum single impurity | 0.0045% |
| | Total impurity | 1.0% | | Total impurity | 0.53% | Total impurity | 0.5% | Total impurity | 0.6% |
| | | | 151212 | Impurity 1 | Undetected | Impurity 1 | Undetected | Impurity 1 | Undetected |
| | | | | Impurity 2 | Undetected | Impurity 2 | 0.0026% | Impurity 2 | 0.0036% |
| | | | | Impurity 3 | 0.011% | Impurity 3 | 0.0037% | Impurity 3 | 0.0070% |
| | | | | Impurity 4 | 0.46% | Impurity 4 | 0.5% | Impurity 4 | 0.5% |
| | | | | Impurity 5 | 0.01% | Impurity 5 | 0.01% | Impurity 5 | 0.02% |
| | | | | Impurity 6 | Undetected | Impurity 6 | Undetected | Impurity 6 | Undetected |
| | | | | Maximum single impurity | 0.012% | Maximum single impurity | Undetected | Maximum single impurity | 0.0062% |
| | | | | Total impurity | 0.66% | Total impurity | 0.6% | Total impurity | 0.7% |
| | | | 151213 | Impurity 1 | Undetected | Impurity 1 | Undetected | Impurity 1 | Undetected |
| | | | | Impurity 2 | Undetected | Impurity 2 | Undetected | Impurity 2 | 0.0035% |
| | | | | Impurity 3 | 0.011% | Impurity 3 | 0.0035% | Impurity 3 | 0.014% |
| | | | | Impurity 4 | 0.35% | Impurity 4 | 0.3% | Impurity 4 | 0.4% |
| | | | | Impurity 5 | Undetected | Impurity 5 | 0.01% | Impurity 5 | Undetected |
| | | | | Impurity 6 | Undetected | Impurity 6 | Undetected | Impurity 6 | Undetected |
| | | | | Maximum single impurity | 0.0085% | Maximum single impurity | 0.0077% | Maximum single impurity | 0.0067% |
| | | | | Total impurity | 0.52% | Total impurity | 0.5% | Total impurity | 0.6% |
| Crystalline form | ModI | | 151211 | ModI | | / | | / | |
| | | | 151212 | ModI | | / | | / | |
| | | | 151213 | ModI | | / | | / | |

| Study item | Limit requirement | | Batch No. | Month 3 | | Month 6 | |
|---|---|---|---|---|---|---|---|
| Related substance | Impurity 1 | 0.17% | 151211 | Impurity 1 | Undetected | Impurity 1 | Undetected |
| | Impurity 2 | 0.17% | | Impurity 2 | Undetected | Impurity 2 | 0.0061% |
| | Impurity 3 | 0.17% | | Impurity 3 | Undetected | Impurity 3 | 0.045% |
| | Impurity 4 | 3.0% | | Impurity 4 | 0.4% | Impurity 4 | 0.4% |
| | Impurity 5 | 0.10% | | Impurity 5 | 0.01% | Impurity 5 | 0.01% |
| | Impurity 6 | 0.10% | | Impurity 6 | 0.02% | Impurity 6 | 0.01% |
| | Maximum single impurity | 0.15% | | Maximum single impurity | Undetected | Maximum single impurity | 0.030% |
| | Total impurity | 1.0% | | Total impurity | 0.5% | Total impurity | 0.7% |
| | | | 151212 | Impurity 1 | Undetected | Impurity 1 | Undetected |
| | | | | Impurity 2 | Undetected | Impurity 2 | 0.0043% |
| | | | | Impurity 3 | Undetected | Impurity 3 | 0.044% |
| | | | | Impurity 4 | 0.5% | Impurity 4 | 0.5% |
| | | | | Impurity 5 | 0.01% | Impurity 5 | 0.01% |
| | | | | Impurity 6 | Undetected | Impurity 6 | Undetected |
| | | | | Maximum single impurity | Undetected | Maximum single impurity | 0.032% |
| | | | | Total impurity | 0.6% | Total impurity | 0.8% |
| | | | 151213 | Impurity 1 | Undetected | Impurity 1 | Undetected |
| | | | | Impurity 2 | Undetected | Impurity 2 | 0.045% |
| | | | | Impurity 3 | Undetected | Impurity 3 | 0.060% |
| | | | | Impurity 4 | 0.37% | Impurity 4 | 0.4% |
| | | | | Impurity 5 | Undetected | Impurity 5 | Undetected |
| | | | | Impurity 6 | 0.01% d | Impurity 6 | Undetected |
| | | | | Maximum single impurity | Undetected | Maximum single impurity | 0.029% |

TABLE 5-continued

The stability evaluation of EOC315 under an accelerated condition (temperature: 40° C. ± 2° C.; relative humidity (RH): 75% ± 5%)

|  |  |  | Total impurity | 0.5% | Total impurity | 0.7% |
|---|---|---|---|---|---|---|
| Crystalline form | ModI | 151211 |  | / |  | ModI |
|  |  | 151212 |  | / |  | ModI |
|  |  | 151213 |  | / |  | ModI |

It can be concluded from the above tables that the crystalline form Mod. I of EOC315 is a thermodynamically stable form.

The produced drug was micronized to increase its bioavailability, and the crystalline form of the micronized drug was still the Mod. I crystalline form except that its crystallinity was decreased.

The invention claimed is:

1. The crystalline form Mod. I of Formula I:

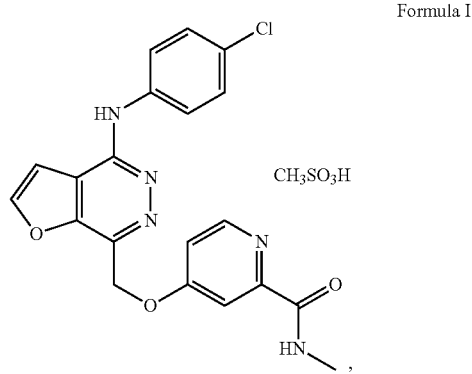

Formula I which has an X-ray powder diffraction diagram with peaks at diffraction angles 2θ of 4.01°±0.1°, 7.85°±0.1°, 9.94°±0.1°, 13.04°±0.1°, 19.08°±0.1°, 19.46°±0.1°, 20.10°±0.1°, 21.82°±0.1°, 22.49°±0.1°, 23.76°±0.1°, 24.26°±0.1°, 27.17°±0.1°, 28.52°±0.1°, and 30.48°±0.1°, when analyzed with X-ray powder diffraction using CuKα radiation.

2. The crystalline form of claim 1, wherein said crystalline form Mod. I has an X-ray powder diffraction diagram substantially the same as the X-ray powder diffraction diagram shown in FIG. 1 when analyzed with the X-ray powder diffraction using CuKα radiation.

3. The crystalline form of claim 1, wherein said crystalline form Mod. I has absorption peaks at 3415 cm$^{-1}$±2 cm$^{-1}$, 3058 cm$^{-1}$±2 cm$^{-1}$, 2805 cm$^{-1}$±2 cm$^{-1}$, 1668 cm$^{-1}$±2 cm$^{-1}$, 1652 cm$^{-1}$±2 cm$^{-1}$, and 1227 cm$^{-1}$±2 cm$^{-1}$, when analyzed with an infrared spectroscopy using KBr pellet.

4. The crystalline form of claim 1, wherein said crystalline form Mod. I has an infrared spectrum substantially the same as the infrared spectrum shown in FIG. 7.

5. The crystalline form of claim 1, wherein said crystalline form Mod. I has a melting point of about 200.6° C.

6. The crystalline form of claim 1, wherein said crystalline form Mod. I has a differential scanning calorimetry thermogram that is substantially the same as that shown in FIG. 3.

7. A process for preparing the crystalline form of claim 1, the process comprising:
   a) dissolving the compound 4-(4-chloroanilino)-7-(2-methylaminocarbonyl-4-oxymethyl) pyridylfuro[2,3-d]pyridazine mesylate in methanol to obtain a solution of the compound, and dissolving methanesulfonic acid methanol to obtain a methanesulfonic acid solution;
   b) adding methanesulfonic acid solution to the solution of the compound;
   c) adding isopropanol and vacuum distilling, and collecting a filter cake after filtration; and
   d) drying the filter cake.

8. A pharmaceutical composition, comprising:
   the crystalline form of claim 1, and
   a pharmaceutically acceptable carrier or excipient.

9. The pharmaceutical composition of claim 8, which is an oral solid preparation.

10. A method for treating cancer, the method comprising:
    administering to a subject in need thereof an effective amount of the crystalline form of claim 1, wherein said cancer is selected from the group consisting of a gastric cancer and a gastroesophageal junction cancer.

11. The method of claim 10, wherein said cancer comprises a solid tumor.

12. The method of claim 10, wherein said cancer comprises an advanced solid tumor and/or a metastatic solid tumor.

13. The method of claim 10, wherein said cancer is gastric cancer, which is an advanced gastric cancer.

14. The method of claim 10, further comprising:
    administering to said subject one or more additional chemotherapeutic agents.

15. The method of claim 14, wherein said one or more additional chemotherapeutic agent is selected from the group consisting of taxol, capecitabine, cisplatin, and gemcitabine.

16. The method of claim 10, further comprising:
    administering to said subject capecitabine and cisplatin.

* * * * *